United States Patent [19]

Orlek et al.

[11] Patent Number: 4,968,691

[45] Date of Patent: Nov. 6, 1990

[54] HETEROCYCLO-SUBSTITUTED AZABICYCLO MUSCANNIC AGONISTS

[75] Inventors: Barry S. Orlek, London; Michael S. Hadley, Sawbridgeworth; Howard E. Rosenberg, Cockfosters; Harry J. Wadsworth, Great Kingshill, all of England

[73] Assignee: Beecham Group P.L.C., Brentford, England

[21] Appl. No.: 320,707

[22] Filed: Mar. 7, 1989

Related U.S. Application Data

[62] Division of Ser. No. 67,018, Jun. 26, 1987.

[30] Foreign Application Priority Data

Jun. 27, 1986 [GB] United Kingdom ................. 8615784
Sep. 17, 1986 [GB] United Kingdom ................. 8622380

[51] Int. Cl.$^5$ ................. A61K 31/33; C07D 417/14; C07D 413/14
[52] U.S. Cl. ................. 514/305; 514/299; 514/361; 514/363; 514/363; 514/364; 514/365; 514/372; 514/374; 514/378; 514/397; 514/406; 546/112; 546/133; 548/127; 548/128; 548/131; 548/134; 548/136; 548/181; 548/214; 548/235; 548/247; 548/336; 548/374
[58] Field of Search ................. 548/214, 181, 235, 247, 548/336, 374, 134, 136, 127, 128, 131; 546/112, 133; 514/299, 305, 374, 378, 365, 372, 397, 406, 361, 362, 363, 364

[56] References Cited

U.S. PATENT DOCUMENTS

| | | | |
|---|---|---|---|
| 2,658,067 | 11/1953 | Duschinsky | 260/294.3 |
| 3,501,471 | 3/1970 | Remers et al. | 260/250 |
| 3,681,363 | 8/1972 | Elkin et al. | 260/293.53 |
| 4,038,402 | 7/1977 | Kaminka et al. | 424/267 |
| 4,203,990 | 5/1980 | Yen | 424/267 |

FOREIGN PATENT DOCUMENTS

| | | |
|---|---|---|
| 1419393 | 5/1983 | Australia . |
| 0239909 | 9/1987 | European Pat. Off. . |
| 307141 | 3/1989 | European Pat. Off. . |
| 316718 | 5/1989 | European Pat. Off. . |

OTHER PUBLICATIONS

H. S. Aaron et al., *J. Amer. Chem. Soc.*, 89, pp. 1431–1437 (1967).
G. Lambrecht and E. Mutschler, *Drug Res.*, 24, p. 1725 (1975).
C. A. Grob and E. Renk, *Helv. Chim. Acta.*, 37, pp. 1689 (1954).
M. J. Martell and T. O. Soine, *J. Pharm. Sci.*, 52, pp. 331–336 (1963).
M. D. Mashkovsky, *Proc. 1st Int. Pharmacol. Meet.*, 7, pp. 359–366 (1963).
D. Spry and H. S. Aaron, *J. Org. Chem.*, 84, pp. 3674–3676 (1969).
L. H. Sternbach and S. Kaiser, *J. Amer. Chem. Soc.*, 74, pp. 2219–2221 (1952) ("Sternbach-I").
L. H. Sternbach and S. Kaiser, *J. Amer. Chem. Soc.*, 74, pp. 2215–2218 (1952) ("Sternbach-II").
B. P. Thill et al., "Azabicyclic Alcohols. V.", *Chem. Abs.*, vol. 70:11 (Mar. 17, 1969): *J. Org. Chem.*, 33:12, pp. 4376–4380 (1968).
K. A. Zaitseva et al., *Chem. Abs.*, vol. 62:11 (May 24, 1965): Farmakol. i Toksikol., 27:6, pp. 686–690 (1964).
J. E. Christie, et al., *Brit. J. Psychiat.*, 138, pp. 46–50 (1981).
P. T. Francis, et al., *N. Engl. J. Med.*, 313, pp. 7–11 (1985).
E. Hollander, et al., *Brit. Med. Bull.*, 42, pp. 97–100 (1986).
E. K. Perry, et al., *Can. J. Neurol. Sci.*, 13, pp. 521–527 (1986).
R. Peterson, *Psychopharmacology*, 52, pp. 283–289 (1977).
Sitaram, et al., *Science*, 201, p. 274 (1978).
Office of Technology Assessment, Publication No. OTA-BA-323 (Washington, D.C: U.S. Government Printing Office) Apr. 1987, pp. 59–62, 104–105.

*Primary Examiner*—Mary C. Lee
*Assistant Examiner*—Peter James Davis
*Attorney, Agent, or Firm*—James F. Haley, Jr.; Leon R. Yankwich; Kenneth H. Sonnenfeld

[57] ABSTRACT

A compound of formula (I) or a pharmaceutically acceptable salt thereof:

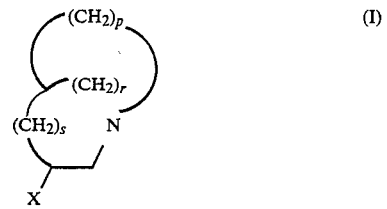

in which X represents a group

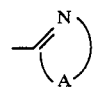

in which p represents an integer of 2 to 4; r represents an integer of 1 or 2; s represents 0 or 1; and A represents a 3-membered divalent residue completing a 5-membered aromatic ring and comprises one or two heteroatoms selected from oxygen, nitrogen and sulphur, any amino nitrogen optionally substituted by a $C_{1-4}$ alkyl group, and when (p,r,s) is (2,2,0) or (2,2,1) any A comprising 2 heteroatoms is optionally C-substituted by a methyl group, and when (p,r,s) is (2,1,0), (2,1,1) or (3,1,0) any A comprising 2 heteroatoms is optionally C-substituted by $C_{1-2}$ alkyl and any A comprising one heteroatom is optionally C-substituted by a methyl group, and wherein compounds of formula (I) having two asymetric centers have the stereo-chemical configuration in which the group X and the $(CH_2)_r$ bridge are on the same side of the plane of the molecule which contains both bridgehead atoms and the ring carbon atom bonded to the group X. The compounds of the present invention enhance acetylcholine function via an action at muscarinic receptors within the central nervous system and are therefore of potential use in the treatment and/or prophylaxis of dementia in mammals.

11 Claims, No Drawings

HETEROCYCLO-SUBSTITUTED AZABICYCLO MUSCANNIC AGONISTS

This is a division of application Ser. No. 067,018, filed June 26, 1987, pending.

This invention relates to compounds having pharmaceutical activity, to a process for their preparation and their use as pharmaceuticals.

3-Methoxycarbonylquinuclidine is described in G. Lambrecht and E. Mutschler, Arzneim. forsh. 24 (11) 1725, 1974 to possess cholinergic activity.

A group of compounds has now been discovered which enhance acetylcholine function via an action at muscarinic receptors within the central nervous system and are therefore of potential use in the treatment and/or prophylaxis of dementia in mammals.

Accordingly, the present invention provides a compound of formula (I. or a pharmaceutically acceptable salt thereof:

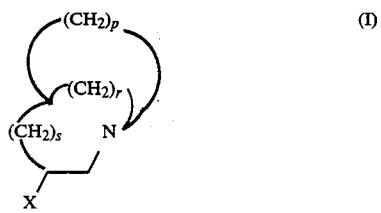

in which X represents a group

in which p represents an integer of 2 to 4; r represents an integer of 1 or 2; s represents 0 or 1; and A represents a 3-membered divalent residue completing a 5-membered aromatic ring and comprises one or two heteroatoms selected from oxygen, nitrogen and sulphur, any amino nitrogen optionally substituted by a $C_{1-4}$ alkyl group, and when (p,r,s) is (2,2,0) or (2,2,1) any A comprising 2 heteroatoms is optionally C-substituted by a methyl group, and when (p,r,s) is (2,1,0), (2,1,1) or (3,1,0) any A comprising 2 heteroatoms is optionally C-substituted by $C_{1-2}$ alkyl and any A comprising one heteroatom is optionally C-substituted by a methyl group.

It will be understood that compounds of formula (I) having two asymetric centres have the stereo-chemical configuration in which the group X and the $(CH_2)_r$ bridge are on the same side of the plane of the molecule which contains both bridgehead atoms and the ring carbon atom bonded to the group X. This configuration will hereinafter be referred to as the exo configuration.

Preferably, any ring carbon bonded to two heteroatoms in X is alkyl-substituted.

Preferably any amino nitrogen is optionally substituted by $C_{1-2}$ alkyl.

Preferably, any alkyl moiety in X is methyl.

Examples of X include 3-methyl-1,2,4-oxadiazol-5-yl, 5-methyl-1,2,4-oxadiazol-3-yl, 5-methyl-1,3,4-oxadiazol-2-yl, 3-methyl-1,2,4-thiadiazol-5-yl, 1,3,4-oxadiazol-2-yl and 1,3-oxazol-2-yl.

Preferred combinations of (p,r,s) include (2,2,0), (2,1,1), (3,1,1), (2,1,0) and (3,1,0).

A subgroup of compounds within formula (I) is of formula (IA):

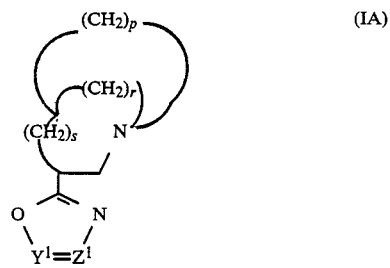

wherein one of $Y^1$ and $Z^1$ represents nitrogen or $CR_1$, where $R_1$ is hydrogen or methyl, and the other represents $CR_2$ where $R_2$ is hydrogen or a methyl group, $R_1$ and $R_2$ not both being methyl.

In compounds of formula (I) within formula (IA), suitable values for X include 3-methyl-1,2, 4-oxadiazol-5-yl, 5-(H or methyl)-1,3,4-oxadiazol-2-yl and 1,3-oxazol-2-y.

Examples of X are as described under formula (I).

Another subgroup of compounds within formula (I) is of formula (IB):

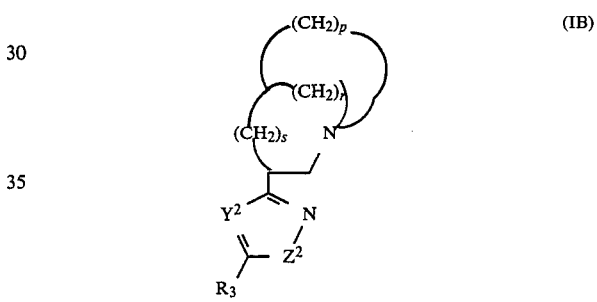

wherein $Y^2$ is nitrogen or CH, $Z^2$ is oxygen or $NR_4$ where $R_4$ is hydrogen or $C_{1-4}$ alkyl, and $R_3$ is hydrogen or methyl, $R_3$ and $R_4$ not both being an alkyl group.

In compounds of formula (I) within formula (IB), suitable values for X include 5-methyl-1, 2,4-oxadiazol-3-yl.

Examples of X are as described under formula (I).

Suitable and preferred values for the remaining variables in formulae (IA) and (IB) are as described for the corresponding variables in formula (I).

The compounds of formula (I) are capable of existing in enantiomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The invention also provides a process for the preparation of a compound of formula (I), or a pharmaceutically acceptable salt thereof, which process comprises:

(a) cyclising a compound of formula (II):

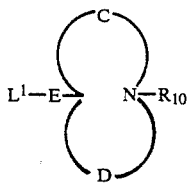
(II)

where $R_{10}$ is hydrogen or an N-protecting group, and either C is one, D is another and E is the remainder of $-(CH_2)_p-$, $-(CH_2)_r-$ and $-(CH_2)_s-CHX'-CH_2-$ or groups convertible thereto, $X'$ is X or a group convertible thereto and $L^1$ is a leaving group, or C is one and E is the other of $-(CH_2)_p-$ and $-(CH_2)_r-$ or groups convertible thereto and D represents $-(CH_2)_s-CHX''-CH_2-$ where $X''$ and $L^1$ together represent $-COO-$, and thereafter, optionally or as necessary and in any appropriate order, converting C, D and E to $-(CH_2)_p-$, $-(CH_2)_r-$ and $-(CH_2)_s-CHX'-CH_2-$, removing any $R_{10}$ protecting group, converting $X'$ to X, interconverting X and/or forming a pharmaceutically acceptable salt, or (b) cyclising a compound of formula (III):

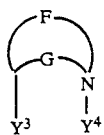
(III)

where F is one and G is the other of $-(CH_2)_p-$ and $-(CH_2)_r-$ or groups convertible thereto, and one of $Y^3$ and $Y^4$ is $-(CH_2)_m-W$ and the other is $-(CH_2)_n-(CO)_qL^2$ where W is an electron withdrawing group, $L^2$ is a leaving group, m is 1 or 2, n is 0 or 1 and q is 0 or 1, with the proviso that, when $Y^4$ is $-(CH_2)_n(CO)_q L^2$, n and q are each 1, and thereafter, optionally or as necessary and in any appropriate order, hydrolysing and decarboxylating the cyclisation product and converting the carbonyl group to $CHX'$ where $X'$ is X or a group convertible thereto, converting W to $X'$ as defined, converting $X'$ to X, converting F and G to $-(CH_2)_p-$ and $-(CH_2)_r-$ as appropriate, interconverting X and/or forming a pharmaceutically acceptable salt, with the proviso that m, n and q are such that the desired compound of formula (I) is obtained.

Examples of leaving groups $L^1$ include halo, such as chloro, and hydroxy. Examples of $L^2$ include those given for $L^1$ or, when q is 1, $C_{1-4}$ alkoxy such as ethoxy. Examples of electron withdrawing groups W include $C_{1-4}$ alkoxycarbonyl and cyano. In the group $-(CH_2)_s-CHX'-CH_2-$, examples of $X'$ include hydroxy and cyano.

In the process variant (a), where $L^1$ is hydroxy and D is $-CHOH-CH_2-$, the cyclisation may be carried out by pyrolysis, by the method of D. O. Spry and H. S. Aaron, J. Org. Chem., 1969, 34, 3674, to yield a compound where $X'$ is hydroxy.

Where E is $-(CH_2)_sCOCH_2-$, the cyclisation may be carried out under basic conditions where $R_{10}$ is benzyl (F. I. Carrol, A. M. Ferguson, and J. B. Lewis, J. Org. Chem. 31, 2957, 1966). The resulting ketone may be reacted with tosylmethyl isocyanide to yield a compound where $X'$ is cyano.

Where $L^1$ and $X''$ together represent $-COO-$, the cyclisation is a rearrangement reaction which can be carried out under acid conditions in a polar solvent, such as hydrogen bromide in ethanol, at ambient temperature, to yield a compound where $X'$ is a carboxy ester group. It is preferred to protect the nitrogen atom with an $R_{10}$ N-protecting group such as benzyl, which may be subsequently removed by hydrogenation over a suitable catalyst such as Pd/C.

In the process variant (b), where $Y^3$ and $Y^4$ both contain carboxy ester groups the cyclisation is a Dieckmann reaction which is catalysed by a base such as potassium t-butoxide at elevated temperature in a solvent such as toluene.

The resulting $\beta$-keto ester is hydrolysed and decarboxylated under conventional conditions such as heating at reflux in dilute hydrochloric acid.

The carbonyl group may then be reduced to an $X'$ hydroxy group with a suitable reducing agent such as sodium borohydride in ethanol at ambient temperature, or sodium in ethanol at elevated temperature, such as the boiling point of the solvent, under an inert atmosphere such as nitrogen, depending upon the stereochemistry required.

Alternatively, the carbonyl group may be converted directly to an $X'$ cyano group with a suitable reagent such as tosylmethyl isocyanide in an inert solvent such as dry dimethoxyethane, at depressed temperature, under basic conditions such as the presence of potassium t-butoxide. wherein q is 0, the cyclisation may be carried out as described in EP-0094742 under basic conditions such as sodium hydride and potassium t-butoxide, in an inert polar solvent such as dimethyl formamide.

The conversions of the groups W and $X'$, and interconversions or X, may be carried out conventionally with regard to the group X, see for example standard text books on heterocyclic chemistry such as 'Comprehensive Heterocyclic Chemistry', A. R. Katritsky and C. W. Rees, Pergamon, 1984.

The $X'$ or W group is first converted, as necessary, to a suitable starting group $X'$ for the chosen conversion reaction to give the required group X.

An $X'$ hydroxy group may be converted to cyano by first converting it to a good leaving group such as mesyloxy or tosyloxy and then displacing it with cyanide ion.

An $X'$ carboxy group may be obtained by conventional de-esterification of an $X'$ or W alkoxycarbonyl group. Where $R_{10}$ is an N-protecting group and $X'$ or W is a benzyloxycarbonyl group, the de-esterification and deprotection steps may conveniently be effected simultaneously by conventional hydrogenation such as described above. Alternatively, an $X'$ carboxy group may be obtained by conventional acid or base hydrolysis of an X or W cyano group.

An $X'$ chlorocarbonyl group may be obtained by treatment of an $X'$ carboxy group with thionyl chloride at elevated temperature.

An $X'$ aminocarbonyl group may be obtained by treatment of an $X'$ chlorocarbonyl group with ammonia. Alternatively, an $X'$ aminocarbonyl group may be obtained by partial alkaline hydrolysis of an $X'$ or W cyano group, for example with an alkali metal hydroxide such as potassium hydroxide, in a polar solvent such as ethanol at elevated temperature. In some cases, it is preferable to carry out the partial hydrolysis using hydrogen peroxide and aqueous sodium hydroxide at room temperature. However, if this alternative procedure is adopted, the bridgehead nitrogen atom must be protected, preferably as a benzyl quaternary salt.

When X represents 3-($C_{1-2}$ alkyl)-1,2,4-oxadiazol-5-yl, reaction of an X' aminocarbonyl group with an acetal of an N,N-dimethyl ($C_{1-2}$)alkyl amide such as the dimethyl or diethyl acetal of N,N-dimethylacetamide, at elevated temperature yields the acyl amidine of formula (IVa):

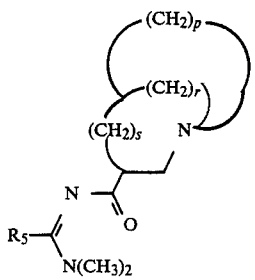

(IVa)

wherein $R_6$ is $C_{1-2}$ alkyl.

The compound of formula (IVa) may then be cyclised with hydroxylamine, in the presence of acid, such as acetic acid, which may also function as the solvent. The reaction may be carried out at ambient temperature the N-hydroxy acyl amidine intermediate isolated and then cyclised at elevated temperature, or alternatively in a one pot procedure without isolation of the intermediate.

Alternatively an X' chlorocarbonyl group may be reacted with a $C_{2-3}$ alkanoic acid amide oxime, such as acetamide oxime, at elevated temperature in an inert, polar solvent such as chloroform, and the resulting substitution product cyclised in an inert solvent such as xylene, again at elevated temperature.

When X represents 5-($C_{1-2}$ alkyl)-1,2,4- oxadiazol-3-yl, the reaction of an X' cyano group may be carried out with hydroxylamine, in a polar solvent such as methanol to yield the corresponding amide oxime of formula (IVb):

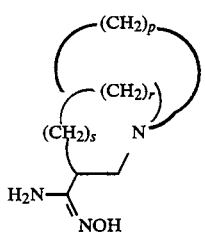

(IVb)

The compound of formula (IVb) may be cyclised using a suitable derivative of a $C_{2-3}$ alkanoic acid, e.g. a derivative of acetic acid such as the anhydride or a trialkylorthoacetate such as triethyl orthoacetate, the acid derivative acting as the solvent, at elevated temperature.

When X represents 5-(H or $C_{1-2}$ alkyl)-1,3,4-oxadiazol-2-yl, an X' carboxy or carboxylic ester group may be converted to the acid hydrazide by conventional procedures. For example, an acid may be converted to a $C_{1-6}$ alkyl ester e.g. methyl, with the appropriate $C_{1-6}$ alkanol e.g. methanol under conventional esterification conditions, and the resulting ester reacted with hydrazine at elevated temperature to give the acid hydrazide of formula (IVc):

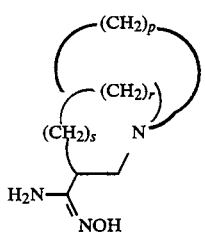

(IVc)

The compound of formula (IVc) may then be cyclised by condensation with a suitable derivative of the appropriate $C_{1-3}$ alkanoic acid $RCO_2H$, e.g. a trialkyl ortho-ester, such as the triethyl ortho-ester, the acid derivative acting as the solvent, at elevated temperature.

When X represents 1,3-oxazol-2-yl, an X' amino carbonyl group may be reacted with vinylene carbonate at elevated temperature in the presence of a strong acid such as polyphosphoric acid, which may also function as the solvent.

When X represents 5-(H or methyl)-1,3-oxazol-2-yl, an X' carboxy group may first be converted to the carboxylic acid chloride and be reacted with a compound of formula $NH_2CH_2CR(OR')_2$, or the X' carboxy group may be reacted directly with the compound of formula $NH_2CH_2CR(OR')_2$ in the presence of a condensing agent such as dicyclohexylcarbodiimide or a chloroformate ester such as ethyl chloroformate, to give a compound of formula (IVd):

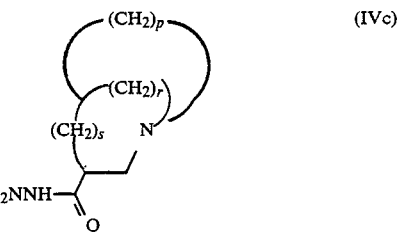

(IVd)

which may be cyclised using a suitable dehydrating agent such as polyphosphoric acid, phosphorus oxychloride, phosphorus pentachloride, sulphuric acid or sulphonyl chloride, preferably polyphosphoric acid.

1,3-oxazol-2-yl groups 4-methyl-substituted may preferably be provided by cyclisation of an X' aminocarbonyl group with propargyl alcohol or the acetate ester thereof, in the presence of a dehydrating agent such as polyphosphoric acid using a catalyst such as $HgSP_4$, at elevated temperature.

Alternative routes to optionally 4-methyl-substituted 1,3-oxazol-2-yl groups include:

(i) the condensation of an X' aminocarbonyl group with the appropriate compound $BrCH_2COR$ at elevated temperature to give a compound of formula (I); or (ii) the reaction of an X' carboxy group under basic conditions with the appropriate compound $BrCH_2COR$ to give a compound of formula (IVe):

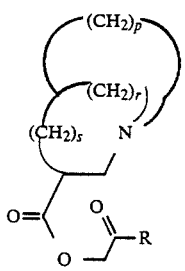

which may be cyclised with ammonium chloride.

During the reaction (i) above, the nitrogen atom of the bicyclic moiety may require protection.

Compounds of formula (I) in which A contains a sulphur atom in place of oxygen may be prepared analogously. A sulphur-containing group X' is obtained by treatment of a carbonyl-containing group X' with either phosphorus pentasulphide or with Lawesson's reagent (S. Scheibye, B. S. Pederson and S. O. Lawesson, Bull. Soc. Chim. Belg., 1978, 87(3), 229). The resulting sulphur-containing group X' may then be converted to the required sulphur-containing group X analogously to the conversion of carbonyl-containing groups.

In formulae (IVa) to (IVe), the variables are as defined in formula (I). In the above description, R represents H, methyl or ethyl as appropriate, and, R' represents $C_{1-6}$ alkyl such as methyl or ethyl.

The invention also provides a process for the preparation of a compound of formula (I), or a pharmaceutically acceptable salt thereof, which process comprises reacting a compound of formula (V):

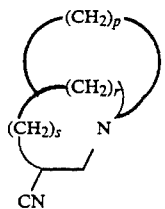

wherein p, r and s are as defined in formula (I), to convert the cyano group into a group X as defined in formula (I), and thereafter, optionally forming a pharmaceutically acceptable salt.

Conversions of the cyano group are as described for conversions of X' cyano groups described above.

Intermediates of formulae (II), (III) and (V) are known compounds (e.g. as described in EP-A-0094742) or may be prepared analogously.

Intermediates of formula (II) where X" and $L^1$ together represent —COO— are described in, for example, Kutnan et al., Coll. Czechoslov. Chem. Comm., 1977, 42, 283 or may be prepared therefrom by conventional hydrogenation of the pyriuine ring over 5% Pt/C, and benzylation of the nitrogen atom by treatment with benzyl bromide and potassium carbonate in dry acetone.

Intermediates of formula (II) where $L^1$ is a leaving group are described in, for example, Spry et al., J. Org. Chem., 1969, 34, 3674 and Hasse et al., Chem. Ber., 1960, 93, 1686.

Intermediates of formula (III) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Novel compounds of formula (IVa) to (IVe) also form part of the invention.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency or administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a cry product for reconstitution with water or other suitable vehicle before use. Such liquid preparations may contain conventional additives sucn as suspending agents, for example sorbitol, syrup, methyl cellulose, gelatin, hydroxyethylcellulose, carboxymethylcellulose, aluminium stearate ge!, hydrogenated edible fats; emulsifying agents, for example lecithin, sorbitan monooleate, or acacia; non-aqueous vehicles (which may include edible oils), for example almond oil fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead or being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound.

However, as a general guide suitable unit doses may be 0.05 to 100 mg. for example 0.2 to 50 mg; and such unit doses may be administered more than once a day, for example two or three times a day, so that the total daily dosage is in the range of about 0.01 to 10 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

The invention also provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) 3-Cyano-1-azabicyclo[2.2.2]octane (D1)

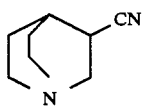

A mixture of 3-quinuclidinone (12.5 g; 0.10 moles), tosylmethyl isocyanide (25.4 g; 0.13 moles) and dry ethanol (10 ml; 0.17 moles) in dry dimethoxyethane (350 ml) was cooled in ice and treated portionwise with potassium t-butoxide (28.0 g; 0.25 moles) while maintaining the temperature between 5° C. and 10° C. After addition was complete the ice bath was removed and stirring was continued for a further 30 min. The reaction was then heated at 4° C. for 2.5 h. After cooling, the precipitate was filtered off and the filtrate concentrated in vacuo. Purification on neutral alumina (Brockmann grade 1) using 2% methanol in ethyl acetate as eluant afforded the title compound as a syrup (10.0 g: 74%) which crystallised on cooling.

DESCRIPTION 2

(±) 1-Azaoicyclo[2.2.2]octane-3-carboxamide (D2)

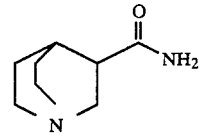

A solution of (±) 3-cyano-1-azabicyclo[2.2.2]octane (D1) (4.1 g; 0.03 moles) in ethanol (250 ml) was treated with potassium hydroxide (7.9 g; 0.12 moles) and the mixture was refluxed under nitrogen for 30 h. After evaporation of solvent in vacuo, the residue was diluted with water (50 ml), saturated with potassium carbonate and extracted into ethyl acetate (4×100 ml). The combined organic extracts were washed with brine, dried (Na₂SO₄) and concentrated to give the title compound as a crystalline solid (3.3 g; 72%). Oxalate salt m.p. 162°–3°.

DESCRIPTION 3

(±) 1-Azabicyclo[2.2.2]octane-3-N-[1-(dimethylamino)-ethylidene]-carboxamide (D3

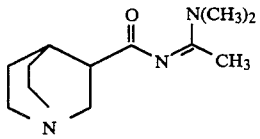

(±) 1-Azabicyclo[2.2.2]octane-3-carboxamide (D2) (0.85 g; 5.5 mmoles) was treated with N,N-dimethylacetamide dimethyl acetal (5 ml) at 12° C. for 1.5 h. Evaporation of excess reagent in vacuo afforded the title compound as an oil (1.3 g) which was used in the next step without further purification.

Ir (Film) 1560 cm$^{-1}$, 1630 cm$^{-1}$

DESCRIPTION 4

(±) 1-Azabicyclo[2.2.2]octane-3-(N-hydroxy)-carboximide (D4)

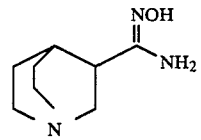

A solution of hydroxylamine in methanol was prepared by addition of hydroxylamine hydrochloride (1.0 g; 14.7 mmoles) to a solution of sodium methoxide generated from sodium (0.34 g; 14.7 mmoles) in methanol (40 ml). To this was added a solution of (±) 3-cyano-1-azabicyclo [2.2.2]octane (D1) (1.0 g; 7.35 mmoles) in methanol (10 ml). The mixture was refluxed for 18 h. After evaporation of solvent in vacuo the residue was extracted with chloroform. Concentration of the organic solution in vacuo, followed by crystallisation of the residue from methanol-ether afforded the title compound (0.57 g: 46%) m.p. 188.5°–190° C.

DESCRIPTION 5

(±)exo-3-Cyano-1-azabicyclo[3.2.1]octane (D5)

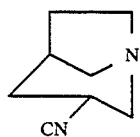

(D5)

1-Azabicyclo[3.2.1]octan-3-one* (2.7 g; 0.022 moles) in dry 1,2-dimethoxyethane (300 ml), under nitrogen, was treated with tosylmethyl isocyanide (3.5 g; 0.029 mmoles) and ethanol (4.6 ml) at 0° C. Potassium t-butoxide (6.8 g, 0.06 moles) was added portionwise at such a rate as to be able to maintain the temperature between 5° C. and 10° C. The reaction mixture was allowed to warm to room temperature over 30min., and then heated at 40° C. for a further 2.5 h. The mixture was cooled and filtered and the residue washed with 1,2-dimethoxyethane. The combined filtrates were concentrated in vacuo and the residual gum purified by column chromatography on alumina eluting with 20% methanol in ethyl acetate. The title compound was obtained as an oil (2.0 g; 66%).

Ir $\nu$ (CN) 2225 cm$^{-1}$, *
D. P. Thill and H. S. Aaron, J. Org. Chem., 1968, 33, 4376.

DESCRIPTION 6

(±) exo-1-Azabicyclo[3.2.1]octane-3-carboxamide (D6)

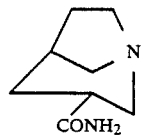

(D6)

A solution of (±) exo-3-cyano-1-azabicyclo[3.2.1]octane (D5) (1.0 g; 0.0074 moles) in ethanol (200 ml) was treated with potassium hydroxide (2.5 g; 0.029 moles) and the mixture was refluxed under nitrogen for 30 h. After evaporation of solvent in vacuo, the residue was diluted with water (50 ml), saturated with potassium carbonate and extracted into ethyl acetate (4×100 ml). The combined organic extracts were washed with brine, dried (Na$_2$SO$_4$) and concentrated to give the title compound as an orange solid (0.36 g; 32%).

DESCRIPTION 7

(±)- exo-1-Azabicyclo[3.2.1]octane-3-N-[1-(dimethylamino)-ethylidene]-carboxamide (D7)

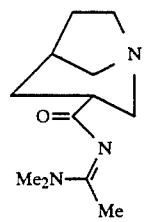

(D7)

(±) exo-1-Azabicyclo[3.2.1]octane-3-carboxamide (D6) (0.36 g) was treated with N,N-dimethylacetamide dimethyl acetal (4 ml) at 120° C. for 1.5 h. Evaporation of excess reagent in vacuo afforded the title compound as an oil which was used in the next step without further purification.

DESCRIPTION 8

(±) 1-Azabicyclo[2.2.2]octane-3-carboxylic acid hydrazide (D8)

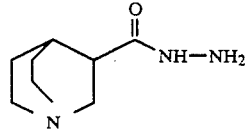

(D8)

(±) Methyl 1-azabicyclo[2.2.2]octane-3-carboxylate* (0.36 g; 2.1 mmoles) and hydrazine hydrate (0.35 ml; 7.0 mmoles) were heated at 120° C. for 2 h. The reaction was diluted with water (10 ml), saturated with potassium carbonate and extracted into chloroform (3×15 ml). Combined organic extracts were dried (Na$_2$SO$_4$) and concentrated to give the title compound as a pale oil (0.36 g; 100%) which was used in the next stage without further purification. *
C. A. Grob and E. Renk, Helv. Chim. Acta, 1954, 37, 1689.

Description 9

(±) exo-6-Cyano-1-azabicyclo[3.2.1]octane (D9)

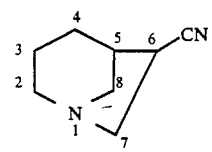

(D9)

A solution of ±1-azabicyclo[3.2.1]octane-6-one* (10 g; 0.08 mole) which had been dried in vacuo, in dry 1,2 dimethoxyethane (400 ml) under an atmosphere of nitrogen was treated with p-tosylmethyl isocyanide (23.4 g; 0.12 mole) and absolute ethanol (6 g; 0.13 mole) at 0° C. with stirring. Potassium t-butoxide (22.6 g; 0.2 mole) was then added at such a rate that the temperature remained below 5° C. When the addition was complete, the solution was allowed to warm to room temperature whilst stirring was continued and, after a further 30 min, the reaction was warmed to 40° C. for 30 min. The reaction mixture was then cooled to 10° C. and filtered. The filtrate was concentrated in vacuo to a gum which was extracted with several portions of ether. The ether extract was separated and concentrated in vacuo to a yellow oil. This was chromatographed on alumina in a gradient of 3–15% methanol in ethyl acetate. The first fraction, eluted with 10% methanol in ethyl acetate, was distilled on a Kugelrohr at approximately 120° C. and 0.1 mm Hg to afford (±) exo-6-cyano-1-azabicyclo[3.2.1]octane (D9) (4.3 g; 40%) as a colourless oil, $^1$H Nmr (CDCl$_3$), δ: 1.38–1.80 (4H, m, 3-CH$_2$, 4-CH$_2$); 2.62 (1H, m, s-CH); 2.80–3.0 (5H, m, 2-CH$_2$, 8-CH$_2$, 6-CH); 3.16 (1H, d,d, J=14 Hz, 5 Hz, 7-CH); *
L. H. Sternbach and S. Kaiser, J.A.C.S., 1952, 74, 2215. 3.36 (1H, d,d,d, J=14 Hz, 8 Hz, 2 Hz, 7-CH). $^{13}$C Nmr (CDCl$_3$), δ: 19.0, 29.8, 32.4, 41.5, 54.4, 57.5, 60.0, 122.7, i.r. νmax 2225 cm$^{-1}$.

The second fraction eluted with 12% methanol in ethyl acetate was distilled on a Kugelrohr at 130° C. and 0.1 mm Hg to afford a semi-solid gum (4.1 g, 38%)

which was recrystallised from pentane to afford (±) endo-6-cyano-1-azabicyclo[3.2.1]octane (1.6 g), m.p. 92°–95° C., ¹H Nmr (CDCl₃), δ: (1.42–1.52 (1H, m) and 1.76–2.0 (3H, m) (together 3-CH₂, 4-CH₂), 2.48 (1H, m, 5-CH), 2.64–2.70 (1H, m) and 2.82–3.02 (4H, m) (together 2-CH₂, 8-CH₂, 6-CH), 3.13 (1H, d,d,d J=2 Hz, 4 Hz, 13 Hz, 7-CH); 3.37 (1H, d,d, J=11 Hz, 13 Hz 7-CH), ¹³C nmr (CDCl₃) δ: 18.6, 27.56, 32.1, 37.9, 55.0, 55.7, 60.8, 120.48, i.r. νmax 2225 cm⁻¹.

DESCRIPTION 10

(±) exo-1-Benzyl-6-cyano-1-azoniabicyclo[3.2.1]octane bromide (D10)

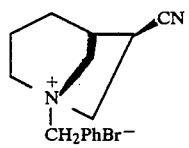

(D10)

A solution of (±) exo-6-cyano-1-azabicyclo[3.2.1]octane (D9) (2 g; 0.015 mole) in ether (50 ml) was treated with benzyl bromide (2.5 g; 0.015 mole) at room temperature overnight. The solution was filtered to afford (±) exo-1-benzyl-6-cyano-1-azoniabicyclo[3.2.1]octane bromide (D10) (4.5 g, 99%) m.p. 250°–253° C., ¹H Nmr (CD₃OD), δ: 1.7–2.0 (4H, m, 3-CH₂ and 4-CH₂), 3.1 (1H, m, 5-CH), 3.3–3.7 (4H, m, 2-CH₂, 8-CH₂), 3.8–4 (2H, m, 6-CH, 7-CH), 4.1–4.2 (1 H, m, 7-CH), 4.725 (1H, d, J=14 Hz) and 4.775 (1H, d, J=14 Hz) (together CH₂Ph), 7.6 (5H, m, Ph).

DESCRIPTION 11

(±) exo-1-Azabicyclo[3.2.1]octane-6-carboxamide (D11)

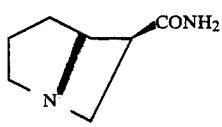

(D11)

A solution of (±) exo-1-benzyl-6-cyano-1-azoniabicyclo[3.2.1]octane bromide (D10) (4.5 g; 0.015 mole) in methanol (250 ml) was treated with hydrogen peroxide (10 ml, 100 vol) and aqueous sodium hydroxide (5 ml, 10%) at room temperature. After 1 h the reaction was adjusted to pH 4 with acetic acid and concentrated in vacuo to a gum. The residue was taken up in methanol (250 ml) and 10% palladium on charcoal (0.5 g) added and stirred under an atmosphere of hydrogen until the uptake of hydrogen ceased. The reaction was then filtered through celite and concentrated in vacuo to a gum. The residue was taken up in saturated aqueous potassium carbonate and extracted exhaustively with chloroform. The chloroform extracts were dried over anhydrous sodium sulphate and concentrated in vacuo to afford (±) exo-1-azabicyclo[3.2.1]octane-6-carboxamide (D11) (1.3 g; 58%) which was recrystallised from ether, m.p. 145°–150° C., 1H nmr (CDCl₃), δ 1.3–1.8 (4H, m, 3-CH₂, 4-CH₂); 2.4 (1H, m, 5-CH); 2.6–3.0 (5H, m, 2-CH₂, 8-CH₂, 6-CH); 3.15 (2H, d, J=4 Hz, 7-CH₂); 6.0 (2H, m, NH₂).

DESCRIPTION 12

(±) exo-3-Cyano-1-azabicyclo[3.3.1]nonane (D12)

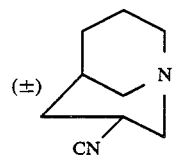

(D12)

A solution of 1-azabicyclo[3.3.1]nonan-3-one⁺ (4.7 g, 0.034 mole) and tosylmethylisocyanide (7.2 g, 0.037 mole) in dry dimethoxyethane (150 ml) at 0° C. was treated with ethanol (3 ml) followed by the portionwise addition of potassium tert-butoxide (8.3 g, 0.075 mole) over 0.5 h. The mixture was stirred at 0° C. for a further 1 h and then at room temperature for 20 h. The mixture was treated with water (25 ml), then saturated by adding solid potassium carbonate and extracted with ethyl acetate. The organic extract was dried (K₂CO₃), filtered and concentrated in vacuo to leave a dark red oil. This was chromatographed on silica gel eluting initially with chloroform, increasing to 8% methanol/chloroform to give the title compound (D12) as a red oil (2.64 g, 52%).

Nmr (CDCl₃) δ: 1.30–2.40 (7H, m, 3×CH₂, CH) 2.80–3.50 (7H, m, 3×CH₂N, CHCN).

IR ν (CN) 2225 cm⁻¹. +
Prepared as described by M. J. Martell Jnr. and T. O. Soine, J. Pharm. Sci., 1963, 52(4), 331.

DESCRIPTION 13

(±) exo-1-Azabicyclo[3.3.1]nonane-3-carboxamide (D13)

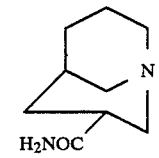

(D13)

A solution of (±) exo-3-cyano-1-azabicyclo[3.3.1-]nonane (D12) (1.20 g, 0.008 mole) in concentrated hydrochloric acid (10 ml) was heated at 100° C. for 3 h. The mixture was evaporated to dryness under reduced pressure, and dried in vacuo overnight. The residue was dissolved in thionyl chloride (12 ml), one drop of DMF added, and the mixture heated under reflux with stirring for 5 h. Excess thionyl chloride was evaporated under reduced pressure and toluene (2×20 ml) used to azeotrope out the final traces. The resulting acid chloride was dissolved in dichloromethane (20 ml) at 0° C., and a solution of ammonia gas in dichloromethane (50 ml) was added with stirring. The organic suspension was then washed with saturated potassium carbonate solution (10 ml), and the aqueous layer then extracted with chloroform (2×50 ml). The organic extracts were combined, dried (Na₂SO₄), filtered and evaporated to dryness under reduced pressure. Column chromatography on basic alumina eluting with chloroform/methanol (0–10%) afforded (±) exo-1-azabicyclo[3.3.1]nonane-3-carboxamide (D13) (0.77 g, 55%), which was used without further purification.

DESCRIPTION 14

(±) cis-4-Benzyl-2-oxo-2a,3,4,5,6,6a-hexahydro-7H-furo[3,4-c]pyridine (D14)

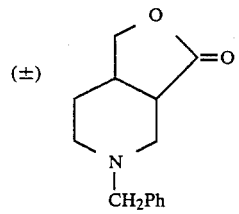

A solution of 2-oxo-7H-furo[3,4-c]pyridine+ hydrochloride salt (9.43 g, 0.055 mole) in a mixture of ethanol (150 ml), water (30 ml) and 5M hydrochloric acid (5 ml) was hydrogenated over 5% Pt/C (400 mg) at 45° C. and 150 psi for 15 h. The catalyst was filtered off through a pad of kieselguhr and the filtrate concentrated in vacuo. The residue was basified with saturated potassium carbonate solution and extracted with chloroform (3×70ml). The organic extract was dried (Na$_2$SO$_4$) and concentrated in vacuo to leave a brown oil (8.5 g), which was dissolved in dry acetone (200 ml) and treated with anhydrous potassium carbonate (16.5 g) and benzyl bromide (7.2 ml). The mixture was stirred at room temperature for 2 h, then diluted with water (400 ml) and extracted with ethyl acetate (3×150 ml). The combined extracts were dried (Na$_2$SO$_4$) and concentrated in vacuo to give a brown oil, which was chromatographed on silica gel eluting with ether to give the title compound (D14) as a pale yellow oil (3.15g, 25%).

+ J Kuthan, L. Musil, V. Jehlicka; Collection Czechoslov. Chem. Comm., 1977, 42, 283.

$^1$H Nmr (CDCl$_3$) δ: 1.52–1.65 (1H, m, 5ax), 1.77–1.86 (1H, m, 5eq), 1.95 (1H, dt, 6ax, J=2.5 Hz and J=13.5 Hz), 2.31 (1H, dd, 2ax, J=5 Hz and J=13.5 Hz), 2.42–2.52 (1H, m, 4ax), 2.59–2.65 (1H, m, 3eq), 2.66–2.73 (1H, m, 6eq), 3.21–3.28 (1H, m, 2eq), 3.45–3.62 (2H, m, CH$_2$Ph), 3.96–4.02 (1H, m, 1×CH$_2$OCO), 4.18–4.25 (1H, m, 1×CH$_2$OCO), 7.20–7.34 (5H, m, PhCH$_2$).

DESCRIPTION 15

(±) exo-Ethyl 1-benzyl-1-azoniabicyclo[2.2.1]heptane-3-carboxylate bromide (D15)

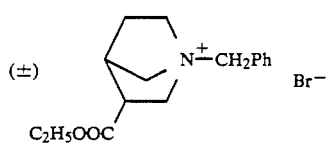

(±) cis-4-Benzyl-2-oxo-2a,3,4,5,6,6a-hexahydro-7H-furo[3,4-c]pyridine (D14, 2.80 g, 0.012 mole) was treated with a saturated solution of hydrogen bromide in ethanol (150 ml) and the mixture stirred at room temperature for 9 days. The mixture was concentrated in vacuo and the residue basified with saturated potassium carbonate solution then extracted with chloroform (3×80ml). The combined extracts were dried and concentrated in vacuo to give the title compound (D15) as a yellow gum (4.0 g, 98%), which was used without purification.

DESCRIPTION 16

(±) exo-Methyl 1-azabicyclo[2.2.1]heptane-3-carboxylate (D16)

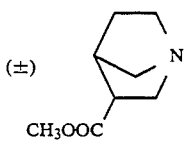

A solution of (±) exo-ethy: 1-benzyl-1-azoniabicyclo[2.2.1]-heptane-3-carboxylate bromide (D15, 4.0 g, 0.012 mole) in ethanol (150 ml) plus glacial acetic acid (2 ml) was hydrogenated over 10% Pd/C (500 mg) at atmospheric pressure and 40° C. until uptake of hydrogen ceased. The catalyst was filtered off through a pad of kieselguhr and the filtrate concentrated in vacuo to leave a beige semi-solid, which was treated with 8M hydrochloric acid (70 ml) and heated under reflux for 2 h. The solution was concentrated in vacuo to give a beige solid, which was treated with methanolic hydrogen chloride (100 ml) and heated under reflux for 30 minutes followed by 2 days at room temperature. The solution was concentrated in vacuo and the residue basified with saturated sodium hydrogen carbonate solution, then extracted with chloroform (3×60 ml). The combined extracts were dried (Na$_2$SO$_4$) and concentrated to give an orange oil, which was distilled in a Kugelröhr apparatus (b.p. approx. 110°–120° C. at 0.4 mm) to give the title compound (D16) (1.3 g, 70%) as a colourless oil. A portion was converted to its oxalate salt and recrystallised from methanol/ether, m.p. 134°–136° C.

Oxalate:- $^1$H Nmr (d$^6$DMSO) δ: 1.65–1.76 (1H, m), 1.90–2.05 (1H, m), 2.85–2.95 (1H, m), 2.95–3.15 (4H, m), 3.22–3.32 (1H, m), 3.35–3.50 (2H, m), 3.68 (3H, s, COOCH$_3$).

Analysis: C$_8$H$_{13}$NO$_2$. C$_2$H$_2$O$_4$.
requires: C: 48.98; H: 6.12; N: 5.71%.
found: C: 48.97; H: 6.17; N: 5.51%.
M.S.: Calculated mass for C$_8$H$_{13}$NO$_2$=155.0946. Observed mass=155.0946.

DESCRIPTION 17

Acetamide Oxime (D17)

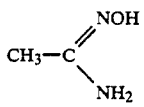

A solution of sodium methoxide (prepared from 2.90 g, 0.126 mole of sodium) in methanol (50 ml) was added dropwise over 10 mins to a stirred solution of hydroxylamine hydrochloride (8.7 g, 0.126 mole) in methanol (100 ml). The mixture was stirred at room temperature for 1 h, then the precipitate was filtered off and the filtrate treated with acetonitrile (6.8 ml, 0.13 mole) and then heated under reflux. After 6 h, a further 6.8 ml of acetonitrile was added and reflux continued for a further 16 h. The solution was then concentrated in vacuo to give the title compound (D17) as a white solid (7.7 g, 83%), m.p. 123°–127° C.

EXAMPLE 1

(±) 3-(3-Methyl-1,2,4-oxadiazol-5-yl)-1-azabicyclo[2.2.2]octane (E1)

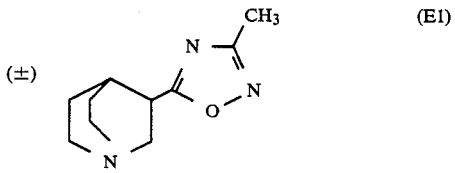

(±) 1-Azabicyclo[2.2.2]octane-3-N-[1-(dimethylamino)-ethylidene]-carboxamide (D3) (1.28 g; 6.0 mmoles) was treated with a solution of hydroxylamine hydrochloride (0.53 g; 7.5 mmoles) in aqueous sodium hydroxide (7.5 ml of 1M NaOH) and then diluted with dioxane (7.5 ml) followed by glacial acetic acid (10 ml). After stirring at room temperature for 30 min., the mixture was heated at 90° C. for 1 h. The reaction was concentrated in vacuo, diluted with water (20 ml) and saturated with potassium carbonate. After extraction into chloroform (4×20 ml) the organic layers were dried (NaSO₄) and concentrated in vacuo to give a crude oil. Removal of polar impurities by extraction of the product into ether and filtration afforded the title compound as an oil (0.85 g; 72%) which was converted into the oxalate salt, m.p. 112°–115° C. (acetone/methanol/ether).

Oxalate: Ir (KBr) $\nu$C=N 1580 cm$^{-1}$.

$^1$H Nmr (d$_6$-DMSO) δ: 1.55–1.85 (2H,m), 1.85–2.10 (2H,m), 2.37 (3H,s), 2.43 (1H,m), 3.15–3.30 (4H,m), 3.50–3.83 (3H,m). $^{13}$C Nmr (CD$_3$OD+d$_6$-DMSO),

δ: 12.08, 20.04, 23.90, 25.63, 33.52, 46.90, 47.22, 49.92, 166.40, 168.34, 180.10.

Analysis: C$_{10}$H$_{15}$N$_3$O. C$_2$H$_2$O$_4$. Requires: C: 50.88; H: 6.05; N: 14.83. Found: C: 50.69; H: 6.37; N: 14.73.

EXAMPLE 2

(±) 3-(5-Methyl-1,2,4-oxadiazol-3-yl)-1-azabicyclo[2.2.2]octane (E2)

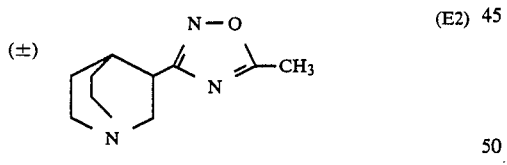

(±) 1-Azabicyclo[2.2.2]octane-3-(N-hydroxy)-carboxiidamide (D4) (0.37 g; 2.2 mmoles) was heated with acetic anhydride (5 ml) at 120° C. for 2 h. Excess reagent was evaporated in vacuo. The residue was treated with water (15 ml) and then saturated with potassium carbonate. After extraction into ethyl acetate (4×20 ml) the combined organic layers were dried (Na$_2$SO$_4$) and concentrated in vacuo. Removal of polar impurities by extraction of product into ether afforded the title compound as a colourless gum which was purified as the oxalate salt.

Oxalate: Ir (KBr) $\nu$C=N 1580 cm$^{-1}$ $^1$H Nmr (d$_6$-DMSO). δ: 1.66–1.82 (2H,m), 1.85–2.15 (2H,m), 2.34 (1H,m), 2.60 (3H,s), 3.16–3.38 (4H,m), 3.40–3.7 (3H,m).

$^{13}$C Nmr (d$_6$-DMSO) δ: 11.99, 18.51, 22.82, 23.98, 31.30, 45.13, 45.44, 47.90, 164.70, 170.12, 177.50.

EXAMPLE 3

(±) exo-3-(3-Methyl-1,2,4-oxadiazol-5-yl)-1-azabicyclo[3.2.1]octane (E3)

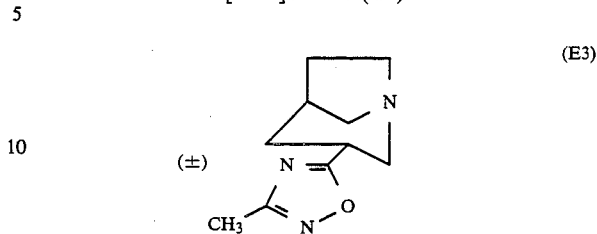

(±) exo-1-Azabicyclo[3.2.1]octane-3-N-[1-(dimethylamino)-ethylidene]-carboxamide prepared as outlined in Description 7 was treated with a solution of hydroxylamine hydrochloride (0.22 g; 3.1 mmoles) in aqueous sodium hydroxide (3.1 ml of 1M NaOH) and then diluted with dioxane (5 ml) followed by glacial acetic acid (10 ml). After stirring at room temperature for 30 min., the mixture was heated at 90° C. for 1 h. The reaction was concentrated in vacuo, diluted with water (20 ml) and saturated with potassium carbonate. After extraction into chloroform (4×50 ml) the organic layers were dried (Na$_2$SO$_4$) and concentrated in vacuo to give a crude oil. Removal of polar impurities by extraction of the product into ether and filtration afforded the title compound as an oil which was converted into the oxalate salt. m.p. 149°–152° (acetone)

Oxalate: Ir $\nu$ (C=N) 1570 c$^{-1}$ MS calculated mass for C$_{10}$H$_{15}$N$_3$O=193.1206 observed mass=193.1216

$^1$H Nmr (d$_6$-DMSO) δ: 1.84–2.04 (2H,m), 2.06–2.2 (2H,m), 2.44 (3H,s), 2.71, (1H,m), 3.1–3.15 (1H,m), 3.4–3.5 (4H,m), 3.6–3.65 (1H,m), 3.86 (1H,heptet).

$^{13}$C Nmr (d$_6$-DMSO) δ: 11.02, 26.69, 27.17, 32.18, 32.63, 48.88, 52.71, 57.26, 164.54, 166.68, 178.26.

EXAMPLE 4

(±) 3-(5-Methyl-1,3,4-oxadiazol-2-yl)-1-azabicyclo[2.2.2]octane (E4)

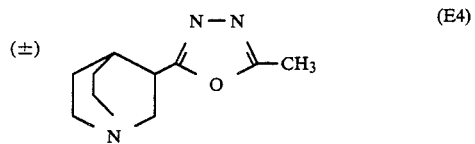

(±) 1-Azabicyclo[2.2.2]octane-3-carboxylic acid hydrazide (D8) (0.36 g; 2.1 mmoles) and triethyl orthoacetate (3 ml) were heated at 120° C. for 2 h. Excess triethyl orthoacetate was evaporated in vacuo and the residue was heated for a further 2 h at 140° C. The reaction was diluted with water (10 ml), saturated with potassium carbonate and extracted into ether (3×15 ml). Combined organic extracts were dried (Na$_2$SO$_4$) and concentrated to give the title compound as an oil (0.29 g; 72%), which was purified as the oxalate salt. m.p. 147°–8° (Acetone-methanol).

Oxalate: Ir (KBr) $\nu$ C=N 1590, 1560 cm$^{-1}$ $^1$H Nmr (d$_6$-DMSO) δ: 1.60–1.80 (2H,m), 1.80–2.08 (2H,m), 2.38 (1H,m), 2.48 (3H,s), 3.15–3.32 (4H,m), 3.52–3.73 (3H,m).

$-^3$C Nmr (d$_6$-DMSO) δ: 10.5, 18.6, 22.5, 23.6, 30.8, 45.1, 45.3, 47.6, 164.3, 164.5, 166.0.

EXAMPLE 5

(±) 3-(1,3-Oxazol-2-yl)-1-azabicyclo[2.2.2]octane (E5)

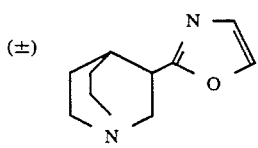 (E5)

A stirred mixture of (±) 1-azabicyclo[2.2.2]octane-3-carboxamide (D2) (2.3 g; 0.015 moles) and vinylene carbonate (1.33 g; 0.016 moles) in polyphosphoric acid was placed in an oil bath at 120° and the temperature was raised to 180° over a period of 45 min. After cooling the reaction was treated with ice and washed with ether (100 ml). The pH of the aqueous solution was adjusted to 9 with 40% sodium hydroxide and potassium carbonate was then added until saturation point. Extraction with ether (4×100 ml) followed by drying (Na$_2$SO$_4$) and concentration in vacuo afforded a crude oil (1.45 g). Purification on neutral alumina (Brockmann grade 1) using a graded eluant of 2%–6% methanol in ethyl acetate produced the title compound as a pale yellow oil (0.74 g; 28%) which was converted into the oxalate salt, m.p. 98°–101° C. (acetone-methanol).

Oxalate: Ir (KBr) ν (C=N) 1560 cm$^{-1}$ $^1$H Nmr (d$_6$-DMSO) δ: 1.55 (1H,m), 1.73 (1H,m), 1.88–2.10 (2H,m), 2.37 (1H,m), 3.12–3.35 (4H,m), 3.55–3.72 (3H,m), 7.24 (1H,s), 8.14 (1H,s).

$^{13}$C Nmr (d$_6$-DMSO) δ18.73, 22.48, 24.24, 32.89, 45.06, 45.38, 48.12, 126.79, 140.47, 163.50, 164.82

Analysis: C$_{10}$H$_{14}$N$_2$O. C$_2$H$_2$O$_4$ requires: C: 53.73; H: 6.01; N: 10.44 found: C: 53.52; H: 6.11; N: 10.30.

EXAMPLE 6

(±) exo-6-(3-Methyl-1,2,4-oxadiazol-5-yl)-1-azabicyclo[3.2.1]octane (E6)

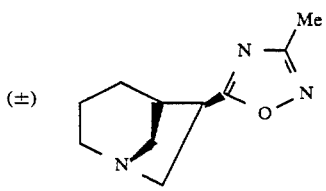 (E6)

A solution of (±) exo-1-azabicyclo[3.2.1]octane-6-carboxamide (D11) (0.4 g; 0.0026 mole) in N,N-dimethylacetamide dimethyl acetal (2.5 g) was heated at 120° C. for 1.5 h. The excess reagent was then evaporated in vacuo and the crude ethylidine carboxamide treated with a solution of hydroxylamine hydrochloride (0.226 g; 0.0033 mole) in aqueous sodium hydroxide (3.2 ml, 1M). Acetic acid (5 ml) and dioxan (5 ml) were added immediately to the stirred reaction mixture and, after 30 minutes at room temperature, the temperature was raised to 90° C. for 1 h. The reaction was then concentrated in vacuo and the residue taken up in aqueous saturated potassium carbonate. The aqueous solution was extracted with chloroform (4×20 ml) and the organic extract was dried over sodium sulphate and concentrated in vacuo to a gum. Chromatography on alumina in a gradient of 3–10% methanol in ethyl acetate afforded 2 fractions. The major second fraction afforded (±) exo-6-(3-methyl-1,2,4-oxadiazol-5-yl)-1-azabicyclo[3.2.1]octane (220 mg, 44%) as a colourless oil. The oxalate salt was prepared by treating the oil (200 mg) in ether with oxalic acid (100 mg) in methanol (1 ml). The oxalate salt (270 mg) was recrystallised from methanol/ether, m.p. 137°–138° C., found: C, 50.63; H, 6.15; N, 15.05%. C$_{12}$H$_{17}$N$_3$O$_5$ requires: C, 50.88; H, 6.05; N, 14.83%, $^1$H nmr (d$_6$-DMSO), δ: 1.7–2.1 (4H, m, 3-CH$_2$, 4-CH$_2$); 2.325 (3H, s, CH$_3$); 2.82 (1H, m, 5-CH); 3.2–3.35 (4H, m, 2-CHhd 2; 8-CH$_2$); 3.6–3.7 (1H, m, 6-H); 3.8–3.95 (2H, m, 7-CH$_2$); 4.6 (2H, br, OH).

EXAMPLE 7

(±) 3-(3-Methyl-1,2,4-thiadiazol-5-yl)-1-azabicyclo[2.2.2]octane (E7)

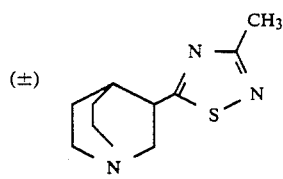 (E7)

Compound E7 is prepared analogously to compound E1 from the nitrile D1. The nitrile is first converted via the carboxamide to the thioamide by treatment with either phosphorus pentasulphide or with Lawesson's reagent (S. Scheibye, B. S. Pederson and S. O. Lawesson, Bull. Soc. Chim. Belg., 1978, 87(3), 229. The thioamide is treated with N,N-dimethylacetamide dimethylacetal at ambient temperature, to yield the thioacyl amidine D18:

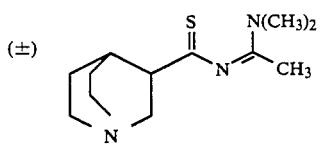 (D18)

which is cyclised by treatment with a suitable hydroxylamine derivative such as hydroxylamine-O-sulphonic acid in the presence of pyridine, in an alcohol such as methanol or ethanol at ambient temperature, or O-(mesitylene sulphonyl)hydroxylamine in dichloromethane at a temperature of 0°–25° C.

EXAMPLES 8

(±) 3-(1,3,4-Oxadiazol-2-y.)-1-azabicyclo[2.2.2]octane (E8)

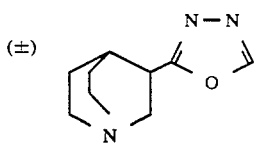 (E8)

A mixture of (±) 1-azabicyclo[2.2.2]octane-3-carboxylic acid hydrazide (D8, 0.5 g, 3.0 mmoles) and triethyl orthoformate (5 ml) was heated under nitrogen at 120° for 8 h. Excess triethyl orthoformate was evaporated in vacuo and the residue was heated at 140° under nitrogen for 2.5 h. The reaction was diluted with water (10 ml) and saturated with potassium carbonate. Extraction into ether (4×10 ml) followed by drying (Na$_2$SO$_4$) and concentration in vacuo afforded the title compound (E8) as a yellow oil (0.13 g; 25%) which was purified as the oxalate salt (mp=146°-148° C. from acetone-methanol).

Oxalate: Ir (KBr) $\nu_{C=N}$ 1565 cm$^{-1}$ $^1$H Nmr (d$_6$-DMSO) δ: 1.50–1.85 (2H, m), 1.85–2.10 (2H, m), 2.40 (1H, m), 3.12–3.35 (4H, m), 3.55–3.85 (3H, m), 9.28 (1H, s).

$^{13}$C Nmr (d$_6$-DMSO) δ: 18.72, 22.53, 23.75, 30.92, 45.10, 45.42, 47.79, 155.10, 164.76, 166.03.

EXAMPLE 9

(±) exo-3-(1,3-Oxazol-2-yl 1-azabicyclo[3.3.1]nonane (E9)

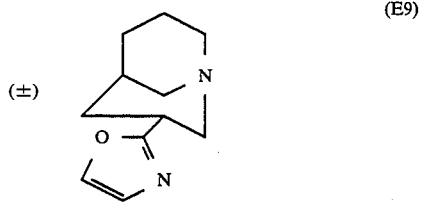

A stirred mixture of (±) exo-1-azabicyclo[3.3.1]nonane-3-carboxamide (D13) (0.77 g, 0.0046 mole) and vinylene carbonate (0.398 g, 0.0047 mole) in polyphosporic acid (PPA) (17 g) was heated in an oil bath at 120° C. and the temperature raised to 140° C. over 1.5 h. After cooling, the mixture was treated with ice (50 ml), allowed to stand for 1 h, and washed with diethyl ether (50 ml). The aqueous solution was adjusted to pH9 with 40% aqueous sodium hydroxide solution, and solid potassium carbonate added until saturation point. The solution was extracted with diethyl ether (4×200 ml), dried (Na$_2$SO$_4$), filtered and evaporated to dryness under reduced pressure to give an orange oil (360 mg). Column chromatography on neutral alumina eluting with methanol (1%)/ethyl acetate gave (±) exo-3-(1,3-oxazol-2-yl)-1-azabicyclo[3.3.1]nonane (E9) (160 mg, 18%) which was converted into the oxalate salt, m.p. 137°–138° C.

Free base: Ir (CHCl$_3$) $\nu$ (C=N) 1565 cm$^{-1}$

Oxalate: $^1$H Nmr (d$_6$-DMSO, 400 MHz) δ: 1.68–2.07 (5H, m, 2×CH$_2$, CH), 2.15–2.30 (3H, m, CH$_2$, CH), 3.30–3.54 (4H, m, 2×CH$_2$N), 3.70–4.02 (2H, m, CH$_2$N), 7.18 (1H, s, oxazole HCN), 8.10 ((1H, s, oxazole HCO).

$^{13}$C Nmr (d$_6$-DMSO, 100 MHz) δ: 18.95, 24.08, 25.62, 30.00, 31.46, 50.05, 51.23, 51.50, 126.67, 139.65, 163.62 and 164.41.

Analysis: C$_{11}$H$_{16}$N$_2$O.C$_2$H$_2$O$_4$ Requires: C: 55.31; H: 6.43; N: 9.92; Found C: 55.16; H: 6.27; N: 9.66.

M.S. Calculated mass for C$_{11}$H$_{16}$N$_2$O=192.1263 observed mass=192.1250.

EXAMPLE 10

(±) exo-3-(3-Methyl-1,2,4-oxadiazol-5-yl)-1-azabicyclo[2.2.1]heptane (E10)

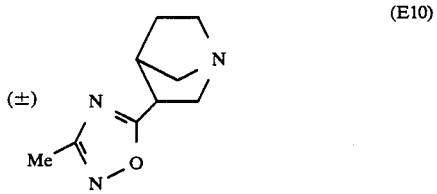

A solution of (±) exo-methyl 1-azabicyclo[2.2.1]-heptane-3-carboxylate (D16) (950 mg, 0.0062 mole) in 8M hydrochloric acid (70 ml) was heated under reflux for 2.5 h, then concentrated in vacuo to give a yellow semisolid. This material was treated with thionyl chloride, (20 ml) and heated under reflux for 4.5 h. The solution was concentrated in vacuo and the residue dissolved in absolute chloroform (130 ml), treated with acetamide oxime (D17, 550 mg, 0.0074 mole) and heated under reflux for 4 h. The reaction mixture was basified with saturated potassium carbonate solution and extracted with chloroform (3×70 ml). The combined extracts were dried (Na$_2$SO$_4$) and concentrated to leave an orange oil, which was treated with xylene (100 ml) and heated under reflux for 1.5 h, using a Dean and Stark head to trap water formed. The reaction mixture was concentrated in vacuo to leave an orange oil, which was chromatographed on silica gel eluting with 2% methanol/chloroform to give the title compound (E10) as a colourless oil. This was converted to its oxalate salt and recrystallised from ethanol/ether to give a white solid (190 mg, 11%) m.p. 116°–120°C.

Oxalate:- $^1$H Nmr (d$_6$-DMSO), 1.75–1.87 (1H, m), 1.95–2.10 (1H, m), 2.35 (3H, s, CH$_3$), 3.10–3.40 (5H, m), 3.53–3.70 (3H, m).

M.S. Calculated mass for C$_9$H$_{13}$N$_3$O=179.1059, Observed mass=179.1041.

BIOLOGICAL ACTIVITY

Radio ligand Binding

Cerebral cortex from Hooded Lister rats (Olac, UK) is homogenised in 2.5 vols ice-cold 50 mM tris buffer pH 7 7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2nM (c. 250,000 cpm) 3H-OXO-M (New England Nuclear).

Non-specific binding of 3H-QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarini agonist 3H-OXO-M and the muscarinic antagonist 3H-QNB. The ratio IC$_{50}$(3H-QNB)/IC$_{50}$(3H-OXO-M) gives an indication of the agonist character of the compound. Agonists typically exhibit a large ration; antagonists typically exhibit a ratio near to unity.

The results are shown in Table 1:

TABLE 1

| Compound+ | [3H]-oxo-M IC$_{50}$ (nM) | [3H]-QNB IC$_{50}$ (nM) |
|---|---|---|
| E1 | 15 | 1840 |
| E2 | 1100 | 17000 |
| E3 | 25 | 1836 |
| E4 | 1000 | 15000 |
| E5 | 630 | 27000 |
| E6 | 41 | 2300 |
| E8 | 2800 | 63000 |
| E9 | 160 | 3100 |
| E10 | 3.5 | 1100 |

+Tested as their oxalate salts

We claim:

1. A compound of formula (I)

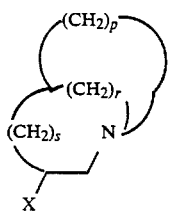  (I)

in which X represents a group

in which p represents an integer of 2 to 4; r represents an integer of 1 or 2; s represents 0 or 1; and A represents a 3-membered divalent residue completing a 5-membered aromatic ring and comprises one heteratom selected from oxygen, nitrogen and sulphur or two heteroatoms selected from sulphur and nitrogen, any amino nitrogen optionally substituted by a $C_{1-4}$ alkyl group, and when (p,r,s) is (2,2,0) or (2,2,1) any A comprising two heteroatomas is optionally C-substituted by a methyl group, and when (p,r,s) is (2,1,1) or (3,1,0) any A comprising two heteroatoms is optionally C-substituted by $C_{1-2}$ alkyl and any A comprising one heteroatom is optionally C-substituted by a methyl group, and wherein compounds of formula (I) having two asymetric centres have the stereo-chemical configuration in which the group X and the (CH$_2$)$_r$ bridge are on the same side of the plane of the molecule which contains both bridge head atoms and the ring carbon atom bonded to the group X.

2. A compound according to claim 1, wherein any ring carbon bonded to two heteroatoms in X is alkyl-substituted.

3. A compound according to claim 1, wherein any amino nitrogen is optionally substituted by $C_{1-2}$ alkyl.

4. A compound according to claim 1, wherein any alkyl moiety in X is methyl.

5. A compound according to claim 1, wherein the azole moiety is 3-methyl-1,2,4-thiadiazol-5-yl or 1,3-oxazol-2-yl.

6. A compound according to claim 1, wherein (p,r,s) is (2,2,0), (2,1,1), (3,1,1), (2,1,0) or (3,1,0).

7. (±) 3-(1,3-oxazol-2-yl)-1-azabicylo[2.2.2]octane, (±) 3-(3-methyl-1,2,4-thiadiazol-5-yl)-1-azabicyclo[2.2.2]octane, or (±) exo-3-(1,3-oxazol-2-yl)-1-azabicyclo[3.3.1]nonane.

8. A compound of formula (I) or a pharmaceutically acceptable salt thereof:

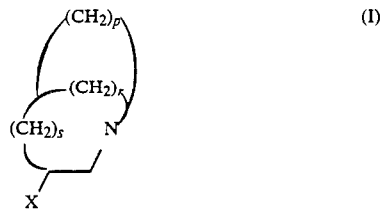  (I)

in which p represents 2, 3 or 4; r represents 1 or 2; and s represents 0 or 1; in which X represents a group

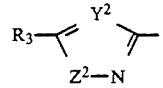

wherein Y$^2$ is CH, or is nitrogen when Z$^2$ is NR$_4$; Z$^2$ ir oxygen or NR$_4$, and R$_4$ is hydrogen or C$_{1-4}$ alkyl; when (p,r,s) is (2,2,0), (2,2,1), (2,1,0) (2,1,1) or (3.1.0) and Y$^2$ is nitrogen, R$_3$ is hydrogen or methyl; and when (p,r,s) is (2,1,0), (2,1,1) or (3,1,0) and Y$^2$ is CH, R$_3$ is hydrogen or methyl, otherwise R$_3$ is hydrogen; and R$_3$ and R$_4$ are not both an alkyl group; and wherein compounds of formula (I) having two assymetric centers have the stereochemical configuration in which the group X and the (CH$_2$)$_r$ bridge are on the same side of the plane of the molecule which contains both bridgehead atoms and the ring carbon atom bonded to the group X.

9. A compound of formula (IA$_i$) or a pharmaceutically acceptable salt thereof:

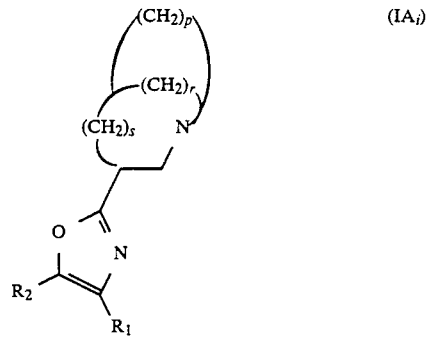  (IA$_i$)

wherein p represents 2,3 or 4; r represents 1 or 2; and s represents 0 or 1; wherein R$_1$ and R$_2$ are both hydrogen or, when (p,r,s) is (2,1,0), (2,1,1) or (3,1,0), R$_1$ and R$_2$ are independently hydrogen or methyl, R$_1$ and R$_2$ not both being methyl; and wherein compounds of formula (IA$_i$) having two asymmetric centers have the stereo-chemical configuration in which the oxazole group and the (CH$_2$)$_r$ bridge are on the same side of the plane of the molecule which contains both bridgehead atoms and the ring carbon atom bonded to the oxazole group.

10. A pharmaceutical composition for the treatment of dementia in mammals comprising a therapeutically effective amount of a compound according to any one of claims 1, 8 or 9 and a pharmaceutically acceptable carrier.

11. A method of treatment and/or prophylaxis of dementia in mammals which comprises administering to an individual a therapeutically effective amount of a compound according to any one of claims 1, 8 or 9.

* * * * *